(12) United States Patent
Camu

(10) Patent No.: US 7,846,486 B2
(45) Date of Patent: Dec. 7, 2010

(54) PASTEURIZATION OR STERILIZATION METHOD AND DEVICE FOR CARRYING OUT SAME

(76) Inventor: Patrice Camu, Le Clos des Cèdres, 17, rue d'Ottersthal, F-67700 Saverne (FR)

( * ) Notice: Subject to any disclaimer, the term of this patent is extended or adjusted under 35 U.S.C. 154(b) by 743 days.

(21) Appl. No.: 11/570,353

(22) PCT Filed: Jun. 9, 2005

(86) PCT No.: PCT/FR2005/050433
§ 371 (c)(1),
(2), (4) Date: Jul. 6, 2007

(87) PCT Pub. No.: WO2006/000728
PCT Pub. Date: Jan. 5, 2006

(65) Prior Publication Data
US 2008/0003135 A1    Jan. 3, 2008

(30) Foreign Application Priority Data
Jun. 14, 2004  (FR) .................................. 04 51173

(51) Int. Cl.
*A61L 2/04* (2006.01)
(52) U.S. Cl. ..................... 426/407; 422/28; 422/32; 422/38; 422/292

(58) Field of Classification Search .................. 422/28, 422/32, 38, 292, 295, 300, 304, 307; 99/452; 426/407
See application file for complete search history.

(56) References Cited

U.S. PATENT DOCUMENTS 2,732,788 A *  1/1956  Meyer .......................... 99/360
3,340,791 A     9/1967  Mencacci et al.

\* cited by examiner

*Primary Examiner*—Sean E Conley
(74) *Attorney, Agent, or Firm*—Egbert Law Offices PLLC

(57) ABSTRACT

The invention relates to a product sterilization or pasteurization method. The inventive method includes: transferring a product from outside to inside a pressurized inlet compartment of a chamber through at least one pressurizing airlock; loading the product onto a conveyor to transfer the product through the chamber from the inlet compartment to an outlet compartment; heating the product by dipping the product in hydrostatic columns while applying variable pressure and temperature; passing the product through an intermediate pressurizing compartment; cooling the product by dipping the product in hydrostatic columns while applying variable pressure and temperature; unloading the product from the conveyor at a pressurized outlet compartment; and transferring the product to the exterior from the outlet compartment through at least one atmospheric pressurization airlock.

10 Claims, 4 Drawing Sheets

PASTEURIZATION OR STERILIZATION METHOD AND DEVICE FOR CARRYING OUT SAME

BACKGROUND OF THE INVENTION (1) Field of the Invention

The present invention relates to a method and the device for implementing the pasteurization or sterilization of products, in particular under flexible or rigid closed packaging.

The purpose of the sterilization and pasteurization are to increase the preservation of food. These operations require a rise in temperature, which is generally followed by a phase of cooling of the product.

During these operations, the rise in temperature creates an increase in pressure inside the packaging. It is then necessary to compensate for this internal pressure by a pressure applied to the outside of the packaging.

(2) Description of the Prior Art

The existing methods and devices thus require a chamber maintained under pressure when sterilization, pasteurization and cooling operations are carried out. An existing device is a chamber in which the products are placed through inlet and/or outlet means. Said chamber is then pressurized, the increase in pressure being carried out as the rise in temperature inside the closed chamber progresses. The temperature and the pressure are then decreased and the products leave the chamber through the inlet and/or outlet means. Such devices are known from the state of the art, such as the autoclaves.

The drawback of these devices is the discontinuous aspect of the method. In order to cope with this discontinuity, a hydrostatic installation was designed to provide the possibility of sterilizing or pasteurizing the products continuously.

The hydrostatic principle consists in causing the products to be sterilized or pasteurized to pass from the top to the bottom of a column of hydrostatic heating fluid, the surface of the fluid column being open to the atmosphere, and therefore subjected to the atmospheric pressure. As the product flows downwards in the column, it is subjected to an increasing pressure applied by the fluid, compensating for the internal increase in pressure due to the rise in temperature. A maximum pressure can be applied in the lower portion of the column and can vary proportionally to the height of liquid in the column. The product must flow upwards under decreasing pressure while being cooled.

A solution for the implementation of this principle consists in placing a median wall in order to separate the column of heating fluid into two, like a siphon, thus forming a circuit within the column. The products are then conveyed from an inlet located at the top of the column, on one side of the wall, to the bottom, being submitted to an increasing pressure, then from the bottom towards an outlet located at the top of the column, on other side of the wall, being submitted to a decreasing pressure.

In order to obtain a sufficient pressure with respect to the sterilization or pasteurization temperature, the height of the installations would be of about ten meters and hence difficult to be installed. Moreover, the temperature of the liquid of a heating column can difficultly vary from the top to the bottom of the column and the products require a phase of cooling under pressure.

In order to cope with these drawbacks, there has been devised an installation in the form of a chamber comprising a hydrostatic heating compartment separated from a hydrostatic cooling compartment by an intermediate pressurizing compartment, this separation being necessary to avoid the thermal exchange and dissipations between the heating and cooling compartments.

The heating and cooling compartments are each comprised of at least one hydrostatic fluid column as described above. In the case of a compartment including several consecutive columns, the pressure corresponding to the height of liquid of a first column is passed on the following column, and so on, from the outside of the chamber under atmospheric pressure to the intermediate compartment.

The intermediate pressurizing compartment serves as a heat insulator between the two other hydrostatic compartments and includes pressurizing means for the intermediate compartment.

Without application of pressure, the levels are balanced on both sides of the median wall of each column. The increase in pressure inside the intermediate compartment applies a pressure on the surfaces of liquid of the columns adjacent to that the compartment. When the pressure applied is sufficient, the level of the column lowers at the side of the partition where the pressure is applied and rises at the other side.

The rising of the level of liquid in the columns creates a pressure on an air column separating two consecutive water columns. This pressure, when it is sufficiently high, causes the level of liquid of the following column to lower and the level located at the other side of the median wall of this column to rise. And so on for any adjacent column.

The pressure applied in the intermediate compartment thus passes on each following column. The pressure in each column depends on the height of liquid to be moved in said column. The pressure applied to each column of liquid decreases from one column to the next one in the direction from the center to the inlet and outlet ends of the chamber, this reduction resulting from the total volume of liquid to be moved being increasingly less as the number of columns diminishes from the intermediate compartment to the inlet or the outlet of the chamber, under atmospheric pressure.

The pressure provided by the intermediate compartment can be increased or decreased according to the needs, according to the type of the products and of their sterilization or pasteurization temperature. However, if this pressure exceeds a maximum value, the level of liquid of the columns will overflow. The maximum pressure applicable within the device is thus increased by the height and the number of columns during manufacture.

The known devices for continuous sterilization or pasteurization thus have the drawback of having a maximum pressure fixed during manufacture and, hence, a maximum pasteurization or sterilization temperature. Under these circumstances, it can happen that for the sterilization or the pasteurization of a line of goods, a large majority of them require an installation the heating compartment of which would include a limited number of hydrostatic columns, while, to cover a minority of products, the counter-pressure to be applied would be such that it would be necessary to substantially increase the number of these columns, which would result into a substantial increase in the cost of the installation.

In U.S. Pat. No. 3,340,791 is disclosed a device for the sterilization of products, in particular glass containers, which is nevertheless without part of these drawbacks. To this end, it comprises a chamber under pressure in which circulates an endless conveyor conveying of products to be sterilized from a chamber under high air pressure to a hydrostatic heating chamber, then through a sterilization chamber, also pressurized, and to a hydrostatic cooling chamber, to finally return into said pressurized chamber. In this connection, said chamber comprises means for loading and unloading said conveyor, which are in the form of a rotary valve under pressure at the inlet and the outlet of the chamber. The hydrostatic chambers are in the form of a compartment, filled with hydrostatic liquid, arranged vertically and a portion of which is lengthened horizontally in order to heat or cool the products under constant pressure. In this connection, it should be noted that these hydrostatic chambers are heated so that at their upper ends, emerging into the sterilization chamber, the liquid is hot, while at their lower end, emerging into the chamber under high air pressure, the liquid is colder. In this way, the products are gradually heated during their passing into the hydrostatic heating chamber and slowly cooled during their being conveyed through the cooling chamber.

Even though it allows to vary the pressure within the chamber by increasing or decreasing the pressure of the highly pressurized chamber, accessible through valves, at the same time as the pressure of the sterilization chamber, this device is aimed at sterilizing solid packaging, such as a glass bottle and is not suitable for flexible or partly flexible packaging. Hence, it has the drawback of applying too high a pressure on the products, the highest in the whole chamber, right from their entering into the pressure chamber, so that flexible packaging can be damaged.

Moreover, the devices of the state of the art generally have the drawback that once the process has been launched, there is little possibility of modifying the parameters, such as the pressure and the temperatures the products are submitted to, but more particularly the sterilization, heating and/or cooling time.

SUMMARY OF THE INVENTION

The object of the invention is to cope with the drawbacks of the state of the art, in particular by providing a device capable of varying the pressure, and hence the temperature, inside the chamber without interrupting the progress of the sterilization or pasteurization process. Moreover, the invention allows to vary the duration of passage of the products inside the chamber, and hence the time during which they are submitted to the pressure and the temperature.

The invention thus allows the sterilization and the pasteurization of products in a broad range and comprising rigid, flexible or partially flexible packaging.

To this end, the invention relates to a method for pasteurizing or sterilizing a product, consisting in:

transferring said product from the outside, under atmospheric pressure, into a pressurized inlet compartment of a chamber through at least one pressurizing airlock;

loading said product onto conveying means ensuring their transfer through said chamber from the inlet compartment to the outlet compartment;

heating the product by dipping it into hydrostatic columns, in order to subject the products to a pressure proportional to their temperature;

causing said product to pass through an intermediate pressurizing compartment;

cooling the product by dipping it into hydrostatic columns, in order to subject the products to a pressure proportional to their temperature;

discharging said product from the conveying means at the level of a pressurized outlet compartment;

transferring said product to the outside from the pressurized outlet compartment through at least one atmospheric pressurization airlock.

According to another feature, the method consists in varying the duration of the passing of the product inside said chamber by varying the length of the path followed by these products in this chamber.

The invention also relates to the device for implementing the preceding method, comprised of a chamber provided, on the one hand, in the form of hydrostatic columns to subject the products to a pressure proportional to their temperature, a heating compartment and a cooling compartment connected by an intermediate pressurizing compartment, said device also including means for conveying the products from an inlet end to an outlet end of the chamber, characterized in that said chamber includes an inlet compartment and an outlet compartment provided with pressurizing means and equipped with at least one pressurization airlock for the products and one atmospheric pressurization airlock for the products, respectively.

According to other features of the invention, several airlocks are connected in parallel and/or in series to the inlet and/or outlet compartments.

In particular, the airlocks substantially form means for loading and unloading the conveying means with products at the height of the inlet and/or outlet compartments.

Advantageously, the device includes means for varying the time of circulation of a product through any of the compartments of the chamber.

In particular, these means for varying the period of circulation consist of means for varying the path followed by said conveying means between the loading and unloading airlocks.

Other features and advantages of the invention will become clear from the following detailed description of non-restrictive embodiments of the invention, with reference to the attached figures.

DETAILED DESCRIPTION OF THE PREFERRED EMBODIMENTS

The present invention thus relates to a method for sterilizing and pasteurizing products and the device for its implementation. It will find its application in the sterilization and pasteurization of products contained in rigid, flexible or partly flexible packagings.

Figure 1:
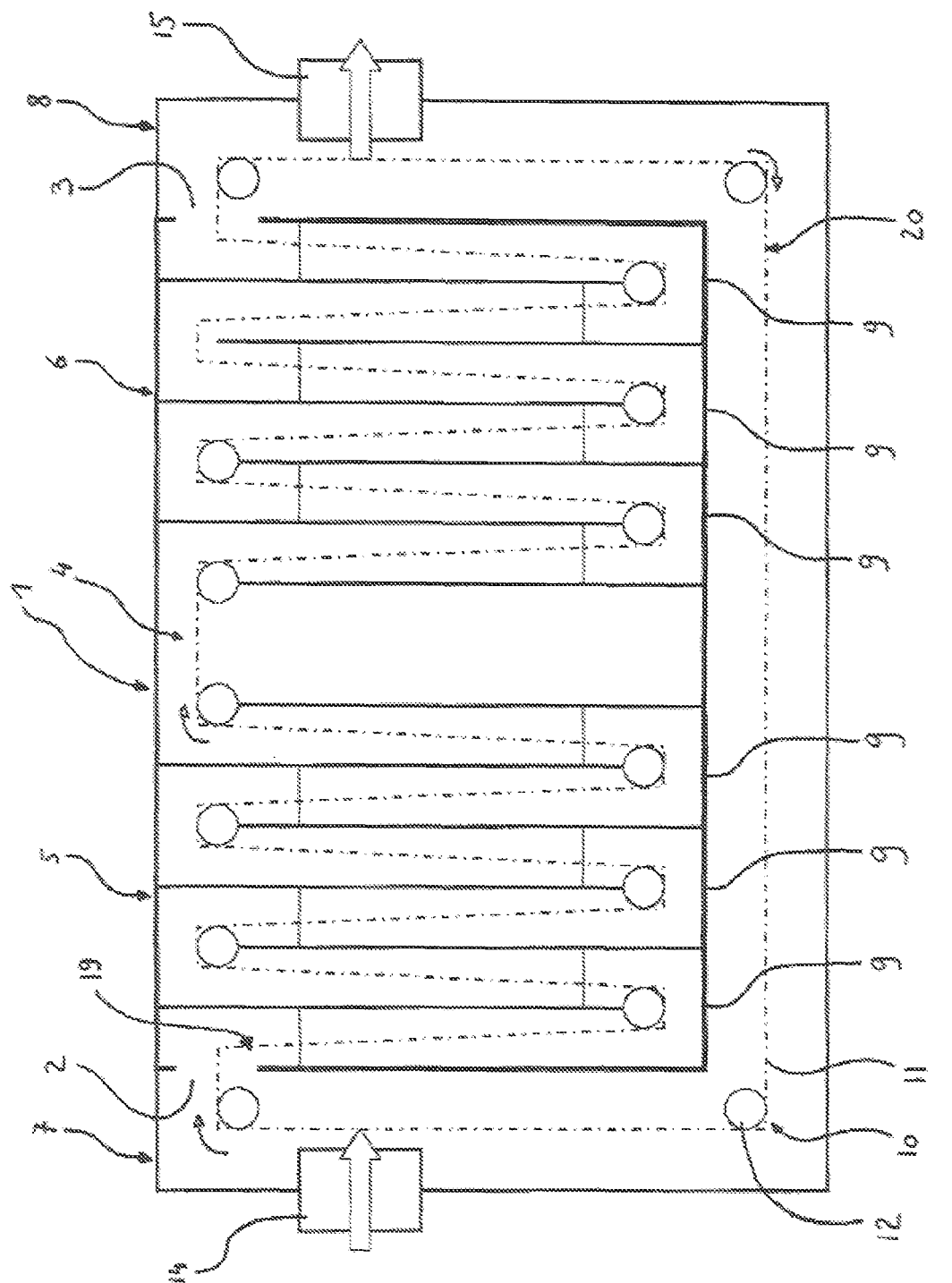
FIG. 1 represents an embodiment of the device according to the invention.

An embodiment of the device according to the invention, visible in FIG. 1, comprises a chamber 1 provided, in the form of at least one hydrostatic column 9, with a heating compartment 5 and a cooling compartment 6. The latter are connected by an intermediate compartment 4, connected to pressurizing means, not shown. The hydrostatic columns 9, forming said heating 5 and cooling 6 compartments, contain a heating liquid and a cooling liquid, respectively.

The device also includes means 10 for conveying the products through various compartments 4, 5, 6, from an inlet end 2 to an outlet end 3 of the chamber 1. Such means 10 can be in the form of an endless transport chain 11, including means for transporting the products, not shown, in the shape of baskets, trays or any other suitable means for transporting the products. This chain 11 is continuously driven by driving means, not shown.

Thus, this chain 11 passes through each of the hydrostatic columns 9 of the heating compartment 5 and the cooling compartment 6, but also the intermediate compartment 4 while passing above adapted return drums 12. Furthermore, it describes a return circuit from the outlet end 3 to the inlet end 2.

In a way particular to the invention, the chamber 1 includes, at its inlet end 2 and its outlet end 3 an inlet compartment 7 and an outlet compartment 8, respectively, each connected to pressurizing means 13.

Figure 2:
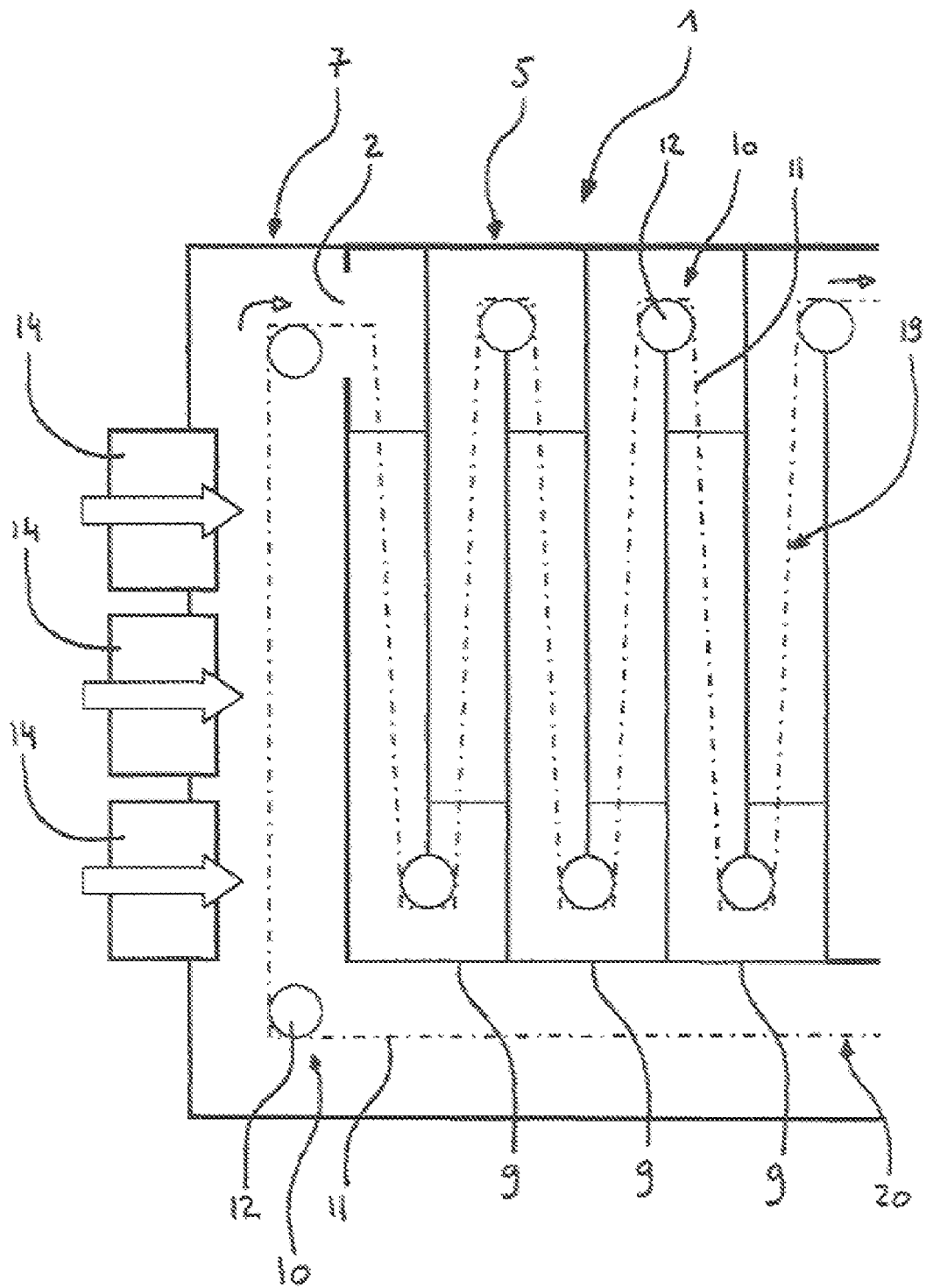
FIG. 2 represents a chamber including pressurizing airlocks connected in parallel to the inlet compartment of the chamber.
Figure 3:
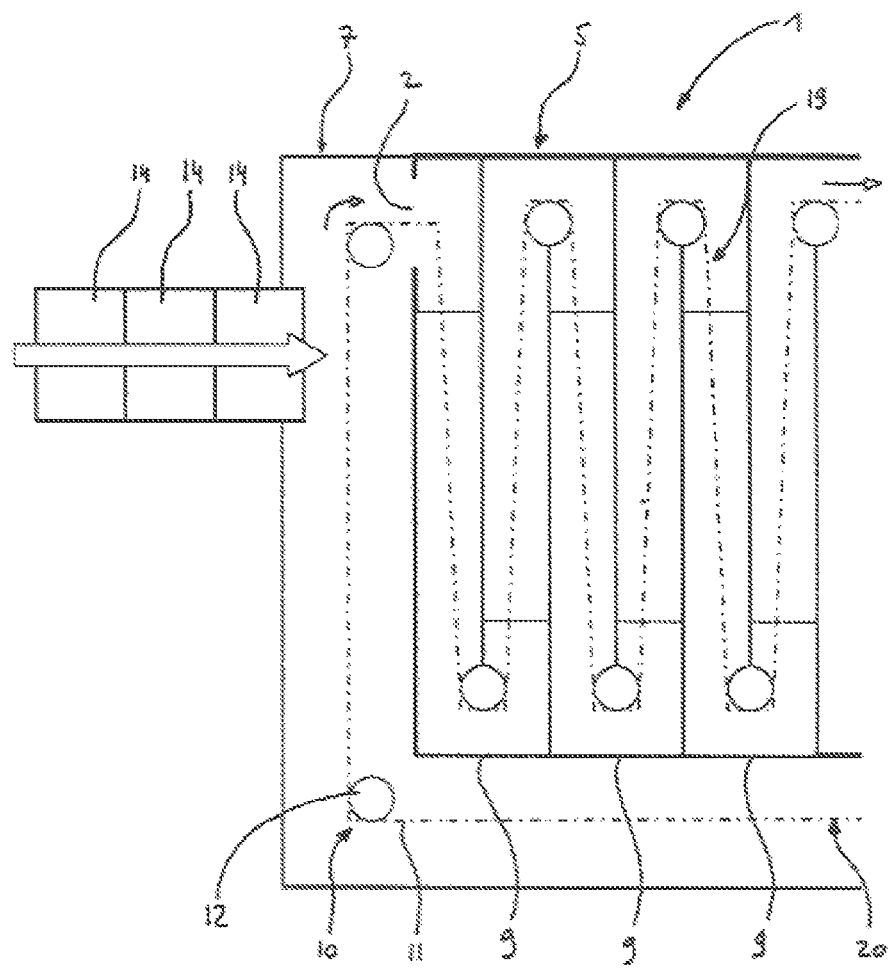
FIG. 3 represents a chamber including pressurizing airlocks connected in series to the inlet compartment of the chamber.

The products penetrate into the inlet compartment 7 and are extracted from the outlet compartment 8 through at least one pressurizing airlock 14 and one atmospheric pressurizing airlock 15, respectively. As can be seen in FIGS. 2 and 3, these airlocks 14, 15 can be placed in parallel or in series reciprocally at the inlet 2 and/or the outlet 3 of the chamber 1. Their arrangement in parallel allows to increase the load capacity and speed of the chain 11 for transporting the products.

The placement of airlock 14, 15 in series allows to gradually increase the pressure applied to the products during their insertion into the inlet compartment 7, while causing these products to circulate from one airlock to another, which then have an increasing pressure with respect to each other, or to gradually decrease the pressure during their extraction from the outlet compartment 8. This stepwise increase of the pressure applied to the products allows to avoid damaging the packagings, in particular in the case of flexible packagings.

In this connection, the pressure the packagings of the products are subjected to increases as the latter are conveyed through hydrostatic columns 9 from the inlet 2 to the intermediate compartment 4, while it gradually decreases from the intermediate compartment 4 to the outlet 3. In this way, since the temperature varies proportionally to the pressure applied on the products and their packagings, the gradual increase in pressure compensates for the effect of the increase in the temperature, in particular the expansion of the contents of the rigid, flexible or partly flexible packagings.

The airlocks 14, 15 thus form, substantially and reciprocally, means for loading and unloading the conveying means 10 with products at the level of the inlet 7 and outlet 8 compartments.

Figure 4:
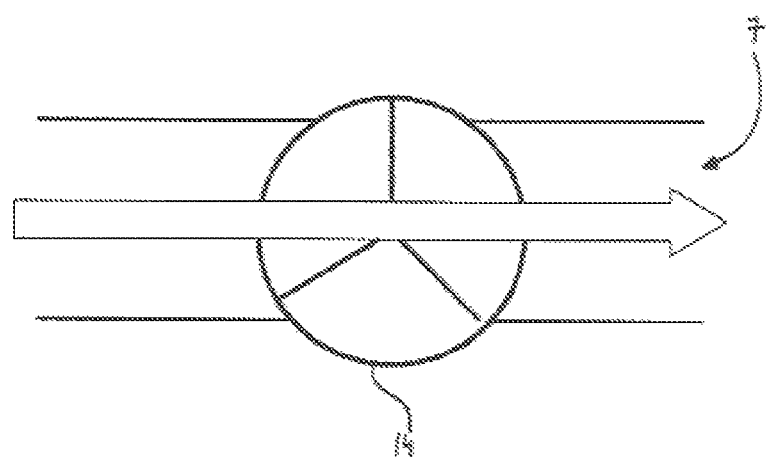
FIG. 4 represents a star-shaped configuration of a pressurizing airlock.

If these airlocks 14, 15 can be with a double door, one can also imagine designing a star-shaped airlock, as can be seen in FIG. 4.

The end compartments 7, 8 of the chamber 1 are thus no longer subjected to the fixed atmospheric pressure, but to a varying pressure. The pressure of the intermediate compartment 4 can thus be equal to the sum of this counter-pressure and the pressures resulting from each hydrostatic column 9 of a compartment 5, 6, and can therefore be modulated at any time. This variation allows the variation of the temperature in the chamber 1, more particularly in the heating 5 and cooling 6 compartments.

The device advantageously comprises means for varying the period of circulation 16 of a product through a compartment of the chamber 1. These means for varying the period of circulation can be formed of means for decelerating or accelerating the speed of displacement of the conveying means 10.

Figure 5:
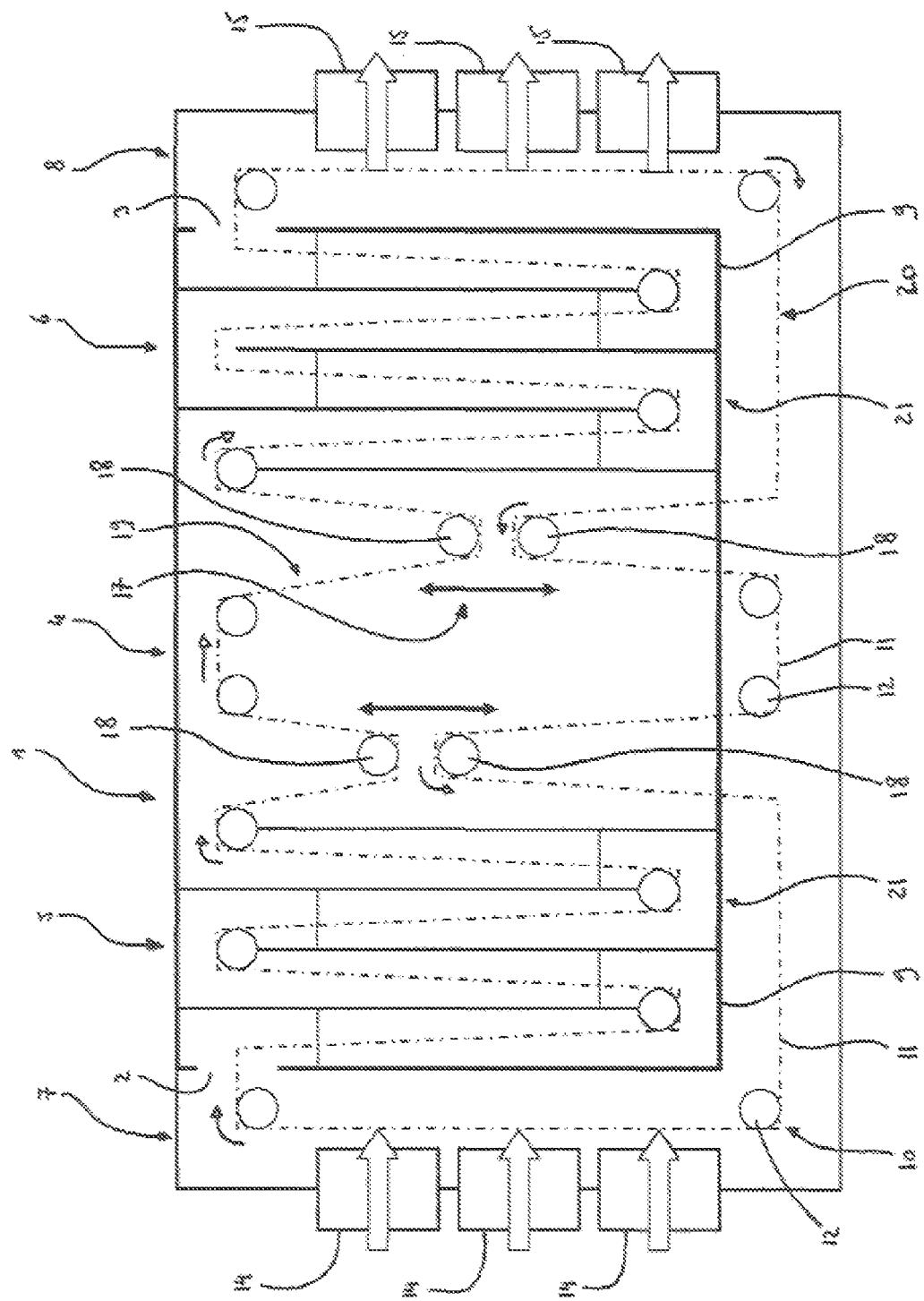
FIG. 5 represents a diagram of a particular embodiment of the invention.

In another embodiment, which can be seen in particular in FIG. 5, these means for varying the period of circulation 16 consist of means for varying 17 the path of displacement of the conveying means 10, more particularly between the loading 13 and unloading 14 airlocks.

In a particular configuration, these means for varying the path 17 are comprised of at least one mobile return drum 18 having a degree of freedom for lengthening or, as the case may be, shortening the length of the chain 11 in either compartment 4, 5, 6, 7, 8.

In an advantageous way, said means for varying the path 17 constitute, in addition, control means for stopping and/or slowing down said chain 11 in front of said loading 14 or unloading 15 airlock without modifying the driving of said chain 11.

In FIG. 5, in which an exemplary embodiment is shown, this or these mobile return drums 18 are designed capable of moving vertically at the level of the intermediate compartment 4. The ascendant displacement of a mobile drum 18 decreases the length of the chain 11, while its descendant displacement increases same.

In this connection, said means for varying the path 17 are defined, more particularly, by at least two mobile return drums 18, one of which is located on the path 19 of the chain 11 between the inlet end 2 and the outlet end 3 of the chamber 1, the other one being located on the return path 20 of the chain 11 between the outlet compartment 8 and the inlet compartment 7.

Thus, lengthening, for example, the path 19 followed by the chain 11 in the chamber 1, while shortening its trajectory on the return path 20, between the outlet compartment 7 and the inlet compartment 8, necessarily results into a deceleration of this chain 11, even the stoppage, in particular in front of the unloading airlocks 15, favoring same. When proceeding in a reverse way, one can achieve the deceleration, even the stoppage of the chain 11, in front of the loading airlock 14, facilitating the transfer of the products from one airlock to the other.

In the same way, by acting on two mobile return drums 18, arranged in an appropriate way in the chamber 1, it is possible to exactly determine the period of transit of the products in the heating compartment 5 and/or the cooling compartment 6.

As is clear from the preceding description, this solution allows to drive the transport chain 11 at a constant speed by suitable driving means that are not subjected to constraints due to the deceleration, the stoppage or the acceleration of said chain 11.

In a particularly advantageous way, a hydrostatic column 9 of the heating 5 and cooling 6 compartments constitutes a module 21, so that it is very easy to adapt the number of these modules of which each of these compartments is comprised.

One will however recall that because of the peculiarity of this invention, namely the presence of the pressurized inlet 7 and outlet 8 compartments, and of the means for varying the period of circulation 16 of a product through any of the compartments 4, 5, 6, 7, 8 of the chamber 1, and this thanks to a control of the path followed by these products in these compartments, the pasteurization or sterilization device according to the invention is capable of being suitable for a very vast range of goods with a limited number of modules 21.

What is claimed:

1. A method for pasteurizing or sterilizing a product in a chamber, the chamber having a continuously driven chain transport chain therein extending through at least a first pair of vertical hydrostatic columns in side-by-side relationship and an intermediate pressurizing compartment and at least a second pair of vertical hydrostatic columns in side-by-side relationship, the chamber having at least one pressurizing airlock opening to a pressurized inlet compartment, the chamber having at least one depressurizing airlock opening to a pressurized outlet compartment, the method comprising:

transferring the product from an exterior of the chamber through the pressurizing airlock and into the pressurized inlet compartment;

loading the product onto the transport chain within the pressurized inlet compartment;

heating the product by moving the product through the first pair of vertical hydrostatic columns by the transport chain such that the product is dipped into each hydrostatic columns, a first column of the first pair of vertical hydrostatic columns having a temperature less than a temperature of a successive column of the first pair of vertical hydrostatic columns, a pressure of the first column and the successive columns being proportional to a respective temperature therein;

passing the product from the first pair of vertical hydrostatic columns through the intermediate pressurizing compartment by the transport chain;

cooling the product by moving the product through the second pair of vertical hydrostatic columns by the transport chain such that the product is dipped into each hydrostatic column of the second pair of vertical hydrostatic columns, a first column of the second pair of vertical hydrostatic columns having a temperature that is greater than a temperature of the successive column of the second pair of vertical hydrostatic columns, a pressure of the first column and the successive column of the second pair of vertical hydrostatic columns being proportional to a respective temperature therein;

discharging the product from the second pair of vertical hydrostatic columns into the pressurized outlet compartment; and transferring the product from the pressurized outlet compartment to an exterior of the chamber through the depressurizing outlet.

2. The method of claim 1, the step of heating comprising:

varying a length of time of passage of the product through the first pair of vertical hydrostatic columns by changing a length of a path followed by the transport chain through the first pair of vertical hydrostatic columns.

3. An apparatus for pasteurizing or sterilizing a product comprising:

a chamber having at least a first pair of vertical hydrostatic columns and at least a second pair of vertical hydrostatic columns with a pressurizing compartment positioned therebetween, the first pair of vertical hydrostatic columns positioned in side-by-side relationship so as to define a heating compartment in said chamber, the second pair of vertical hydrostatic columns positioned in side-by-side relationship so as to define a cooling compartment in said chamber, said chamber having an inlet end and an outlet end, said chamber having an inlet compartment positioned between said inlet and the first pair of vertical hydrostatic columns, said chamber having an outlet compartment positioned between the second pair of vertical hydrostatic columns and said outlet end, said inlet end having at least one pressurizing airlock therein, said outlet end having at least one depressurizing airlock formed therein, the pressurizing airlock opening to said inlet compartment, the depressurizing airlock opening to said outlet compartment;

a continuously-driven endless transport chain suitable for conveying the product from said inlet end to said outlet end of said chamber, said transport chain following a path through said inlet compartment and through the first pair of vertical hydrostatic columns and through said intermediate pressurizing compartment and through the second pair of vertical hydrostatic columns and through said outlet compartment, said transport chain positioned adjacent to the pressurizing airlock and adjacent to the depressurizing airlock; and a pressurizing means connected to said chamber for introducing pressure into said chamber.

4. The apparatus of claim 3, said pressurizing airlock comprising a plurality of airlocks opening to said inlet compartment, said depressurizing airlock comprising another plurality of airlocks opening to said outlet compartment.

5. The apparatus of claim 4, each of the airlocks having a star-shaped configuration.

6. The apparatus of claim 3, said pressurizing airlock suitable for allowing the product to be placed on said endless transport chain in said inlet compartment, said depressurizing airlock suitable for allowing the product to be removed from said endless transport chain in said outlet compartment.

7. The apparatus of claim 3, further comprising:

a means for varying a duration of the product in at least one of said inlet compartment, said heating compartment, said intermediate pressurizing compartment, said cooling compartment and said outlet compartment, said means for varying comprising at least one mobile return drum movable so as to lengthen or shorten a path traversed by said endless transport chain.

8. The method of claim 7, said means for varying for slowing down or stopping said endless transport chain adjacent said pressurizing airlock and said depressurizing airlock.

9. The apparatus of claim 7, said means for varying comprising at least two mobile return drums, one of the two mobile return drums positioned on said endless transport chain between said inlet end and said outlet end of said chamber, another of the two mobile return drums positioned on said endless transport chain between said outlet compartment and said inlet compartment.

10. The apparatus of claim 3, said inlet compartment and said outlet compartment each being a module, said module comprised of at least one vertical hydrostatic column.

* * * * *